United States Patent
Shigematsu et al.

(10) Patent No.: US 6,455,731 B2
(45) Date of Patent: Sep. 24, 2002

(54) PROCESS FOR PRODUCING A HIGH PURITY AROMATIC POLYCARBOXYLIC ACID

(75) Inventors: Ryusuke Shigematsu; Masayoshi Hayashi, both of Ibaraki-ken; Shinichi Nagao; Jitsuo Oishi, both of Okayama-ken; Akio Hashimoto, Ibaraki-ken, all of (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 09/858,487

(22) Filed: May 17, 2001

(30) Foreign Application Priority Data

May 25, 2000 (JP) ........................................ 2000-154793
Dec. 27, 2000 (JP) ........................................ 2000-397491

(51) Int. Cl.7 ............................................... C07C 51/42
(52) U.S. Cl. ........................ 562/486; 562/485; 562/494
(58) Field of Search ................................ 562/485, 486, 562/494

(56) References Cited

U.S. PATENT DOCUMENTS 6,194,609 B1 * 2/2001 Abrams et al. ............. 562/486

FOREIGN PATENT DOCUMENTS

EP 0 787 712 * 8/1997

* cited by examiner

Primary Examiner—Paul J. Killos
Assistant Examiner—Zachary C. Tucker
(74) Attorney, Agent, or Firm—Antonelli, Terry, Stout & Kraus, LLP (57) ABSTRACT

A process for producing a high purity aromatic polycarboxylic acid by purify a crude aromatic polycarboxylic acid in accordance with the steps of (I) forming an amine salt of an aromatic polycarboxylic acid from the crude polycarboxylic acid and an amine, (II) continuously decomposing the salt in a salt decomposition reactor in operations of (i) supplying an aqueous solution of the amine salt of an organic polycarboxylic acid formed in the step of forming a salt, (ii) removing the amine and water by distillation under heating and (iii) taking out a slurry containing crystallized aromatic polycarboxylic acid, and (III) separating and recovering crystals of the aromatic polycarboxylic acid from the slurry which is taken out in the step of decomposing the salt. A high purity aromatic polycarboxylic acid having excellent hue and large particle diameters can be produced from a crude aromatic polycarboxylic acid industrially with stability at a low cost of production in accordance with a process having a simple construction.

14 Claims, 2 Drawing Sheets

PROCESS FOR PRODUCING A HIGH PURITY AROMATIC POLYCARBOXYLIC ACID

BACKGROUND OF THE INVENTION

1. Field of the Invention

The present invention relates to a process for producing a high purity aromatic polycarboxylic acid useful as a material for polyesters, polyamides, polyimides and liquid crystalline polymers and, more particularly, to a process for producing a high purity naphthalenepolycarboxylic acid and a high purity biphenylpolycarboxylic acid which are not easily purified, heretofore.

2. Description of the Prior Art

Aromatic polycarboxylic acids are commercially important substances as chemical intermediates and have a wide demand as materials of polyesters, polyamides, polyimides and liquid crystal polymers which are used for fibers, bottles, films and electronic applications.

The aromatic polycarboxylic acids industrially used in a wide range of applications are, for example, terephthalic acid, isophthalic acid, phthalic acid, trimellitic acid, pyromellitic acid, 2,6-naphthalenedicarboxylic acid, 4,4'-biphenyldicarboxylic acid, 1,4,5,8-naphthalenetetracarboxylic acid and 3,3'4,4'biphenyltetracarboxylic acid.

As the process for producing an aromatic polycarboxylic acid, processes in which an aromatic polyalkylhydrocarbon such as xylene, a dialkylnaphthalene, a dialkylbiphenyl, a tetraalkylnaphthalene and a tetraalkylbiphenyl is oxidized with molecular oxygen at a high temperature and a high pressure in the presence of a heavy metal such as Co and Mn and a bromine compound in acetic acid as the solvent or oxidized with the air in the presence of nitric acid or chromic acid, are known. The aromatic polycarboxylic acid obtained by the oxidation reaction contains impurities such as monocarboxylic acids and aldehyde which are intermediate products of the oxidation reaction, addition products of bromine and metal components which are derived from the catalyst and coloring substances having unknown structures.

Recently, necessity for recycling plastic materials such as polyesters is increasing and recycle and reuse of materials are conducted, for example, by decomposition of PET bottles. However, in general, aromatic polycarboxylic acids obtained by the above decomposition contain impurities such as colored components and foreign substances.

When the aromatic polycarboxylic acids containing impurities are used as materials in the polymerization with diols and diamines, the obtained resins exhibit inferior physical and mechanical properties such as inferior heat resistance, mechanical strength and dimensional stability. Therefore, such aromatic polycarboxylic acids cannot be used as the materials for polyesters, polyamides and polyimides. In general, crude aromatic polycarboxylic acids obtained by oxidation are colored yellow or black and cannot be used for applications requiring transparency such as bottles and films without further treatments. Moreover, since the crude aromatic polycarboxylic acids are in the form of particles having small diameters, handling is not easy and problems tend to arise during polymerization. Therefore, the process for producing a high purity aromatic polycarboxylic acids having improved hue and particle diameters industrially advantageously has been studied for a long time.

In general, purification of an organic compound is conducted in accordance with distillation, crystallization, adsorption or a combination of these operations. However, since aromatic polycarboxylic acids have a temperature of self-decomposition lower than the boiling point, the purification by distillation is substantially impossible. Moreover, since aromatic polyearboxylic acids have poor solubility in solvents ordinarily used in industrial production, the purification by crystallization cannot be easily conducted. In particular, naphthalenepolycarboxylic acid and biphenylpolycarboxylic acids have very poor solubility in various solvents and no industrially advantageous processes for producing a high purity naphthalenepolycarboxylic acid or a high purity biphenylpolycarboxylic acid have been established.

Many processes in which a salt is formed from an amine and an aromatic polycarboxylic acid and the purification is conducted in accordance with a treatment such as crystallization and adsorption, have Been proposed. For example, in Japanese Patent Application Laid-Open No. Heisei 7(1995)-118200, a process in which a salt of an amine and naphthalenedicarboxylic acid is purified by crystallization from a mixed solvent of water and an alcohol, is disclosed. In Japanese Patent Application Laid-Open No. Heisei 10(1998)-53557, a process in which an amine salt of naphthalenedicarboxylic acid is purified by crystallization in a mixed solvent of water and an aliphatic or alicyclic ketone, is disclosed.

The amine salt of an aromatic polycarboxylic acid thus obtained is decomposed by heating and the aromatic polycarboxylic acid is crystallized. As the process for this treatment, for example, processes in which an amine salt of naphthalenedicarboxylic acid is decomposed by blowing steam at 140° C. into an aqueous solution of the amine salt at 130° C. or by flushing an aqueous solution of the amine salt with boiling under an ordinary pressure from a heated and pressurized tank are disclosed in Japanese Patent Application Laid-Open No. Showa 50(1975)-142542. Processes in which an amine salt of terephthalic acid is decomposed by heating an aqueous solution of the amine salt under the refluxing condition at an ordinary pressure or by blowing steam at 135° C. into an aqueous solution of the amine salt are disclosed in Japanese Patent Application Laid-Open No. Heisei 6(1994)-293696.

The above processes for producing an aromatic polycarboxylic acid is not industrially advantageous due to the following reasons:

(1) In the process in which an aqueous solution is flushed with boiling under an ordinary pressure from a heated and pressurized tank and the process in which an aqueous solution is heated under the refluxing condition under an ordinary pressure, the rate of decomposition is small due to a low temperature for the decomposition and the processes are economically disadvantageous since a great amount of water must be vaporized.

(2) In the process in which an amine salt is decomposed by blowing steam into an aqueous solution of the amine salt, a great amount of steam is required to obtain an aromatic polycarboxylic acid in a high yield since the concentration of the amine salt in the aqueous solution decreases and the process is not economically advantageous.

Decomposition of an amine salt of an aromatic polycarboxylic acid was conducted by the present inventors in accordance with the industrially most popular process in which heat is supplied from the jacket of a salt decomposition reactor. It was found that the decomposition of the amine salt of an aromatic polycarboxylic acid could not be continued for a long time with stability since crystals of the amine salt of an aromatic polycarboxylic acid were formed, tightly stuck to the wall surface of the salt decomposition reactor and covered the surface of heat transfer.

In the process in which the salt of an aromatic polycarboxylic acid and an amine is purified and the purified amine salt is decomposed, the utility cost is great since great amounts of steam and heating gas are required. When the concentration of the slurry is increased to decrease the amount of energy consumption, a high purity aromatic polycarboxylic acid in the form of particles having large diameters cannot be obtained.

SUMMARY OF THE INVENTION

The present invention has an object of providing a process for industrially producing a high purity aromatic polycarboxylic acid having excellent hue and large particle diameters at a low cost of production for a long time with stability in accordance with a process having a simple construction by decomposing an amine salt of an aromatic polycarboxylic acid obtained from a crude aromatic polycarboxylic acid.

As the result of extensive studies by the present inventors to achieve the above object, it was found that a high quality aromatic polycarboxylic acid can be easily produced in accordance with a process having a simple construction and the consumption of energy can be decreased remarkably when a salt of a crude aromatic polycarboxylic acid and an amine is formed and an aqueous solution of the amine salt of the aromatic polycarboxylic acid is continuously decomposed by heating.

As the first invention, the present invention provides a process for producing a high purity aromatic polycarboxylic acid by purifying a crude aromatic polycarboxylic acid in accordance with following steps:

(I) a step of forming a salt which comprises forming an amine salt of an aromatic polycarboxylic acid from the crude polycarboxylic acid and an amine;

(II) a step of decomposing a salt which comprises continuously conducting in a salt decomposition reactor three operations of (i) supplying an aqueous solution of the amine salt of an organic polycarboxylic acid formed in the step of forming a salt, (ii) removing the amine and water by distillation under heating and (iii) taking out a slurry containing crystallized aromatic polycarboxylic acid; and (III) a step of separating crystals which comprises separating and recovering crystals of the aromatic polycarboxylic acid from the slurry which is taken out in the step of decomposing a salt.

It was also found by the present inventors that an amine salt of an aromatic polycarboxylic acid could be decomposed with stability for a long time in accordance with a process having a simple construction without sticking of the aromatic polycarboxylic acid to the wall surfaces of the heat exchanger or the salt decomposition reactor when a slurry in the salt decomposition reactor which comprised an aqueous solution of the amine salt of an aromatic polycarboxylic acid and the aromatic polycarboxylic acid formed by the decomposition was circulated through a heat exchanger and heated, the pressure of the slurry in the heat exchanger was kept at the vapor pressure of the slurry or higher, the slurry was introduced into the salt decomposition reactor, the amine salt was decomposed by removing a mixture of the amine and water by distillation and the aromatic polycarboxylic acid was crystallized.

As the second invention, the present invention provides a process for producing a high purity aromatic polycarboxylic acid by purifying a crude aromatic polycarboxylic acid in accordance with (I) a step of forming a salt which comprises forming an amine salt of an aromatic polycarboxylic acid from the crude polycarboxylic acid and an amine, (II) a step of decomposing a salt which comprises (i) conducting in a salt decomposition reactor operations of supplying an aqueous solution of the amine salt of an aromatic polycarboxylic acid formed in the step of forming a salt, (ii) removing the amine and water by distillation under heating and (iii) taking out a slurry containing crystallized aromatic polycarboxylic acid, and (III) a step of separating crystals which comprises separating and recovering crystals of the aromatic polycarboxylic acid from the slurry which is taken out in the step of decomposing a salt, wherein in the step of decomposing a salt, the slurry in the salt decomposition reactor which comprises the aqueous solution of the amine salt and the aromatic polycarboxylic acid formed by the decomposition is circulated through a heat exchanger, heat is supplied in the heat exchanger while a pressure of the slurry is kept at a vapor pressure of the slurry or higher, a mixture of the amine and water is removed by distillation in the salt decomposition reactor, and the aromatic polycarboxylic acid is crystallized in the salt decomposition reactor.

DETAILED DESCRIPTION OF THE INVENTION

The aromatic polycarboxylic acid purified in accordance with the process of the present invention is a compound having at least one aromatic ring and at least two carboxyl groups bonded to the aromatic ring. Examples of the aromatic ring include rings of aromatic hydrocarbons such as benzene, naphthalene and biphenyl.

Examples of the aromatic polycarboxylic acid include terephthalic acid, isophthalic acid, phthalic acid, trimellitic acid, trimesic acid, pyromellitic acid, naphthalenedicarboxylic acid, naphthalenetricarboxylic acid, naphthalenetetracarboxylic acid, biphenyldicarboxylic acid, biphenyltricarboxylic acid and biphenyltetracarboxylic acid.

In the present invention, naphthalenepolycarboxylic acids and biphenylpolycarboxylic acids are preferable among these compounds. Examples of the naphthalenepolycarboxylic acid include naphthalenedicarboxylic acid, naphthalenetricarboxylic acid and naphthalenetetracarboxylic acid. Examples of the biphenylpolycarboxylic acid include biphenyl dicarboxylic acid, biphenyltricarboxylic acid and biphenyltetracarboxylic acid.

As described above, in general, purification by distillation of aromatic polycarboxylic acids is substantially impossible since these acids have temperatures of self-decomposition lower than the boiling points. Purification by crystallization cannot be easily conducted since aromatic polycarboxylic acids have small solubility in solvents which are industrially widely used. The process of the present invention can be advantageously used, in particular, for purification of naphthalenepolycarboxylic acids and biphenylpolycarboxylic acids which are not easily dissolved into various solvents.

In the present invention, the process for producing the aromatic polycarboxylic acid is not particularly limited. In general, a derivative of the aromatic hydrocarbon described above which is substituted with a plurality of functional groups which are easily oxidized and give carboxyl groups is used as the raw material. Examples of the functional group include alkyl groups such as methyl group, ethyl group and isopropyl group, formal group and acetyl group. A crude aromatic polycarboxylic acid can be obtained by oxidation of the derivative of the aromatic hydrocarbon.

Naphthalenedicarboxylic acid which is useful as the raw material of polyesters, polyurethanes and liquid crystal polymers is obtained by oxidation of a dialkylnaphthalene with molecular oxygen in the presence of an oxidation catalyst. The crude naphthalenedicarboxylic acid thus obtained contains coloring substances, metals of the oxidation catalyst and organic impurities such as formylnaphthoic acid which is an intermediate product of the oxidation reaction, trimellitic acid formed by decomposition of the naphthalene ring, naphthalenedicarboxylic bromide formed by addition of bromine and naphthalenetricarboxylic acid.

Biphenyldicarboxylic acid which is useful as the raw material of polyesters, polyamides and liquid crystal polymers is obtained by oxidation of a dialkyl-biphenyl with molecular oxygen in the presence of an oxidation catalyst. The crude biphenyldicarboxylic acid thus obtained contains coloring substances, metals of the oxidation catalyst and organic impurities such as formylbiphenyl carboxylic acid, alkylbiphenylcarboxylic acids and biphenylmonocarboxylic acid derived from the raw material.

In the present invention, the crude aromatic polycarboxylic acid is purified after being converted into an amine salt.

As the amine component constituting the amine salt, aliphatic amines and alicyclic amines are preferably used. Examples of the amine include aliphatic amines such as methylamine, dimethylamine, trimethylamine, ethylamine, diethylamine, triethylamine, propylamine, dipropylamine, tripropylamine, isopropylamine, diisopropylamine, triisopropylamine, butylamine, dibutylamine, tributylamine and 2-ethylhexylamine; and alicyclic amines such as piperidine, N-methylpiperidine, pyrrolidine, ethyleneimine and hexamethyleneimine.

Among these amines, tertiary aliphatic amines which have great rates of decomposition in decomposition of amine salts and can be easily recovered such as trimethylamine, triethylamine, tripropylamine and triisopropylamine are preferable. From the standpoint of availability and easiness of handling, triethylamine and trimethylamine are more preferable.

Figure 1:
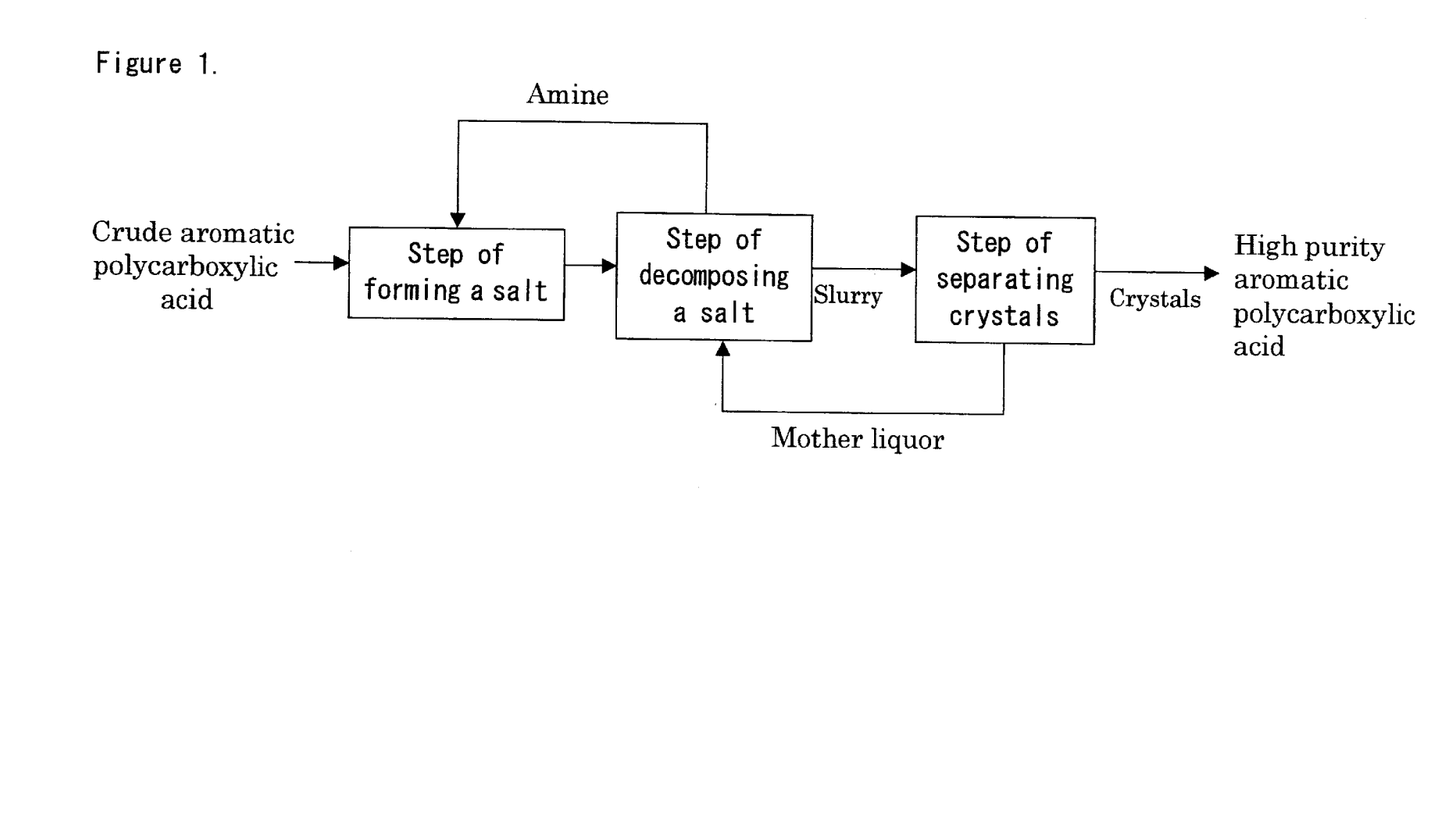
FIG. 1 shows a diagram exhibiting the process for producing a high purity aromatic polycarboxylic acid of the first invention.

In the first invention, the process for producing a high purity aromatic polycarboxylic acid by purification of a crude aromatic polycarboxylic acid comprises (I) a step of forming a salt, (II) a step of decomposing a salt and (III) a step of separating crystals. The relation between the steps is shown in FIG. 1.

In the step of forming a salt, a crude aromatic polycarboxylic acid and an amine are used as the raw materials and an amine salt of the aromatic polycarboxylic acid (referred to as an amine salt, hereinafter) is formed. A purification operation may be conducted, where necessary. The step of decomposing a salt comprises continuously conducting in a salt decomposition reactor three operations of (i) supplying an aqueous solution of the amine salt, (ii) removing the amine and water by distillation under heating and (iii) taking out a slurry containing the aromatic polycarboxylic acid. The step of separating crystals comprises separating and recovering crystals of a high purity aromatic polycarboxylic acid from the slurry which are taken out in the step of decomposing a salt in accordance with an operation of solid-liquid separation. It is preferable that the mother liquor remaining after the crystals have been separated and recovered is recycled and reused as a material in the step of decomposing a salt.

In the first step of forming a salt, the amine salt is formed from the crude aromatic polycarboxylic acid and the amine. For example, the amine salt can be formed by dissolving the aromatic polycarboxylic acid and the amine in water or by mixing and stirring the aromatic polycarboxylic acid and the amine in the presence of water and an aqueous solvent selected from acetone, an alcohol, pyridines and amides so that a portion or the entire amount of the amine salt of the aromatic polycarboxylic acid are dissolved.

The amine is used in an amount necessary for neutralizing the crude polycarboxylic acid or more. For the industrial application, it is economical that the amount of the amine is 1.0 to 1.2 equivalent per 1 equivalent of the carboxyl group in the crude aromatic polycarboxylic acid.

The aqueous solution of the amine salt obtained above may be used as the raw material in the step of decomposing a salt without further treatments or, when impurities such as coloring substances, organic impurities and metal impurities are contained in great amounts, the purification process described in the following may be conducted.

As the purification process used in the step of forming a salt, for example, a process in which the amine salt is dissolved in water and then treated with an adsorbent such as active carbon, a process in which catalytic reduction is conducted in the presence of a catalyst of a metal of the VIII Group such as Pt and Pd, a process in which the amine salt is dissolved in a solvent selected from water, alcohols, pyridines, ketones and amides and then crystallized by cooling or concentration, or a process in which the amine salt is dissolved in water and then recrystallized by adding a solvent having small ability of dissolving the amine salt such as acetone and pyridine, may be conducted. Coloring substances and organic impurities contained in the crude aromatic polycarboxylic acid can be removed in accordance with the above processes. The above purification processes may be conducted singly or in combination of two or more. In any of the processes, it is preferable that, when insoluble substances such as foreign substances and metal impurities are found when the amine salt is dissolved, the insoluble substances are removed in accordance with an operation of solid-liquid separation before or after the purification.

In the second step of decomposing a salt, the aqueous solution of the amine salt of the aromatic polycarboxylic acid obtained in the first step of forming a salt is heated and a slurry containing crystals of the aromatic polycarboxylic acid are obtained by removing the amine and water by distillation. In order to increase the yield, it is preferable that a mother liquor obtained in the third step of separating crystals is recycled and reused as a material in the step of decomposing a salt. It is also preferable that the amine removed by distillation are recycled and reused in the step of forming a salt. The concentration of the aromatic polycarboxylic acid in the aqueous solution of the raw material is 5 to 60% by weight and preferably 10 to 40% by weight although the concentration may be different depending on the type of the aromatic polycarboxylic acid and the type of the amine. When the concentration is smaller than the above range, it is necessary that a great amount of water be removed by distillation and disadvantage arises with respect to the energy. When the concentration is greater than the above range, the quality of the obtained aromatic polycarboxylic acid deteriorates. Thus, such concentrations are not preferable.

In the step of decomposing a salt, three operations of (i) supplying an aqueous solution of the amine salt of the polycarboxylic acid, (ii) removing the amine and water by distillation under heating and (iii) taking out a slurry containing crystallized aromatic polycarboxylic acid are conducted in a salt decomposition reactor. It is preferable that the three operations are conducted completely continuously. It is also possible that the three operations are conducted intermittently at a specific time interval. The amount of the content in the salt decomposition reactor can be kept in a specific range by adjusting the amounts of substances in a manner such that the sum of the amounts of distilled substances from the gas phase and the amount of the slurry taken out is the same as the amount of the supplied raw materials within a specific range of the time. The amine removed by distillation is recovered and reused in the step of forming a salt after being purified, where necessary.

As for the temperature of decomposing the salt, a low temperature causes a decrease in the rate of decomposition of the salt and is economically disadvantageous. A high temperature may occasionally cause degradation and coloring of the amine and the aromatic polycarboxylic acid. Therefore, the temperature of decomposing the salt is, in general, in the range of 100 to 250° C., preferably in the range of 110 to 210° C. and more preferably in the range of 120 to 160° C. The pressure is, in general, in the range of 0 to 2 MPa although the pressure depends on the composition of the content at the temperature of decomposition.

In the step of decomposing a salt, the aqueous solution of the amine salt of the aromatic polycarboxylic acid is heated and the amine and water are removed by distillation, so that the aromatic polycarboxylic acid is crystallized and a slurry is formed. In the present invention, the concentration of the slurry in the salt decomposition reactor is defined by B/A and the ratio of decomposition of the amine salt is defined by B/C when the total amount by weight of the slurry taken out of the salt decomposition reactor per unit time is represented by A, the amount by weight of crystals of the aromatic polycarboxylic acid in the slurry taken out is represented by B and the amount by weight of the aromatic polycarboxylic acid in the aqueous solution of the amine salt of the aromatic polycarboxylic acid supplied to the step of decomposing a salt is represented by C.

In the step of decomposing a salt of the first invention, the concentration of the crystals of the aromatic polycarboxylic acid in the slurry taken out of the salt decomposition reactor is in the range of 5 to 50% by weight and preferably in the range of 10 to 30% by weight. Crystals of the aromatic polycarboxylic acid having large diameters can be obtained by decomposing the amine salt in a suitable concentration of the slurry. When the concentration of the slurry exceeds the above range, the diameter of crystals decreases. When the concentration of the slurry is smaller than the above range, the amount of recycled materials increases and productivity decreases.

In the first invention, the fraction of decomposition of the amine salt is in the range of 20 to 80% and preferably in the range of 30 to 70%. By maintaining the fraction of decomposition of the amine salt at a suitable value and by recycling the mother liquor after separating crystals of the aromatic polycarboxylic acid in the step of separating crystals, the consumption of energy in the entire process can be decreased and the high purity aromatic polycarboxylic acid can be obtained efficiently. When the fraction of decomposition of the amine salt is smaller than the above range, the amount of the recycled aromatic polycarboxylic acid increases and economic disadvantage arises. When the fraction of decomposition of the amine salt exceeds the above range, the concentration of the slurry exceeds the suitable range and the quality of the product deteriorates.

In the first invention, by heating the aqueous solution of the amine salt of the aromatic polycarboxylic acid and continuously decomposing the salt so that the concentration of the slurry and the fraction of decomposition of the amine salt in the salt decomposition reactor are kept in the above ranges, the operation can be conducted industrially with stability. The high quality aromatic polycarboxylic acid having particles having large diameters can be obtained and separation and purification of the crystals are facilitated. The consumption of energy in the entire process can be decreased and the cost of production can be remarkably decreased. Thus, the high quality aromatic polycarboxylic acid can be obtained industrially advantageously.

In the third step of separating crystals, the slurry taken out in the step of decomposing a salt is separated into crystals and a mother liquor by an apparatus for solid-liquid separation. The crystals are washed with water and dried and the high purity aromatic polycarboxylic acid can be obtained. The amount of water used for washing is 0.1 to 10 parts by weight and preferably 0.5 to 3 parts by weight per 1 part by weight of the crystals of the aromatic polycarboxylic acid. When the amount of water is less than the above range, a portion of the impurities are left remaining without being washed away.

To increase the yield, it is preferable that the entire amounts or at least portions of the mother liquor obtained after separation of the crystals and the washing liquid are recycled and reused as raw materials in the step of decomposing a salt. The mother liquor and the washing liquid which are recycled and reused may be used as the solvent for the salt formed in the step of forming a salt or may be supplied to the salt decomposition reactor without further treatments in combination with the fresh raw materials.

In the step of decomposing a salt and the step of separating crystals described above, crystals of the high quality aromatic polycarboxylic acid having large diameters can be obtained and washing of the crystals can be facilitated by the above procedures. Therefore, organic impurities and coloring substances can be removed efficiently by the purification. When organic impurities and coloring substances are accumulated in the mother liquor of the aromatic polycarboxylic acid, a portion of the mother liquor may be suitably separated and disposed or the mother liquor may be recycled to the step of forming a salt so that the impurities are concentrated and removed to the outside of the system by the purification operation in the step of forming a salt.

In the first invention, by the continuous decomposition of the amine salt and the separation of crystals in the suitable conditions, the amount of utilities such as steam and cooling water can be decreased and the process becomes economically advantageous. Moreover, by recycling and reusing the amine removed by distillation and the mother liquor obtained after separation of the aromatic polycarboxylic acid, a high yield can be easily achieved in the entire process.

As will be clearly shown in the examples described later, in accordance with the process of the first invention, the high purity aromatic polycarboxylic acid can be obtained from the crude aromatic polycarboxylic acid remarkably advantageously with respect to energy consumption. By continuously decomposing the aqueous solution of the amine salt by heating in a manner such that the concentration of the slurry and the fraction of decomposition of the amine salt are kept in the specific ranges, the high quality aromatic polycarboxylic acid having particles having large diameters can be obtained continuously. By recycling and reusing the mother liquor separated from the crystals, the high purity aromatic polycarboxylic acid can be obtained easily in a high yield.

The second invention relates to a process mainly used in (II) the step of decomposing a salt of the first invention. The major part of the apparatus for conducting the process of the second invention is constituted with a salt decomposition reactor and a heat exchanger.

In the second invention, a slurry in the salt decomposition reactor comprising the aqueous solution of the amine salt of the aromatic polycarboxylic acid and crystals of the aromatic polycarboxylic acid formed by the decomposition (referred to as a circulating slurry, hereinafter) is circulated through a heat exchanger. Heat is supplied in the heat exchanger kept at a pressure which is the same as or higher than the vapor pressure of the slurry. In the salt decomposition reactor, a mixture of the amine and water is removed by distillation and the aromatic polycarboxylic acid is crystallized. The slurry containing the aromatic polycarboxylic acid is suitably taken out and the object aromatic polycarboxylic acid is obtained after a suitable operation of separation.

The type of the salt decomposition reactor is not particularly limited as long as the reactor has a structure such that the mixture of the amine and water can be removed by distillation and the slurry can be circulated to the outside of the reactor.

The slurry in the salt decomposition reactor which contains crystals of the aromatic polycarboxylic acid is transferred to the heat exchanger. The method of transfer is not particularly limited. In general, a pump is used. When a pump is used, the type of the pump is not particularly limited. In general, a centrifugal pump which can transfer in a great amount to a great head is used. When a centrifugal pump is used, it is preferable that the speed of rotation of an impeller is kept low so that fracture of the crystals of the aromatic polycarboxylic acid by the impeller is suppressed. For this purpose, an inverter may be disposed in the pump and the speed of rotation of the impeller may be controlled. Fracture of the crystals can be suppressed also by expanding the gap between the impeller and the casing.

The type of the heat exchanger used in the second invention is not particularly limited and a heat exchanger of the double tubular type, the multi-tubular type or the plate type may be used. Due to the excellent efficiency of heat transfer and easiness of cleaning, the heat exchanger of the multi-tubular type is preferable. When the flow speed in the heat exchanger is small, crystals of the aromatic polycarboxylic acid tend to stay still and stick to the surface of heat transfer. Therefore, it is necessary that portions in the heat exchanger where the crystals may stay still be kept as small as possible. It is preferable that the linear velocity of the slurry in the heat exchanger is 1 m/sec or greater.

In the second invention, it is preferable that the pressure of the slurry in the heat exchanger is kept at a specific value or higher. The method for keeping the pressure at a specific value or higher is not particularly limited. When the slurry is circulated by a pump, the pressure inside the heat exchanger can be kept at a specific value or higher by an orifice or a valve, preferably a control valve (referred to as CV, hereinafter) which can control the flow speed or the pressure, disposed at a position at the outlet of the heat exchanger.

By keeping the pressure of the circulating slurry at the outlet of the heat exchanger higher than the vapor pressure of the circulating slurry at the temperature at the outlet of the heat exchanger, decomposition of the amine salt by vaporization in the heat exchanger can be suppressed and sticking of the aromatic polycarboxylic acid to tubes of the heat exchanger and piping can be suppressed.

The pressure of the slurry at the outlet of the heat exchanger is kept higher than the vapor pressure of the slurry at a temperature at the outlet of the heat exchanger and the difference in the pressure is +0.01 MPa or greater and preferably in the range of +0.02 MPa to +0.5 MPa. When the difference in the pressure is smaller than the above range, crystals of the aromatic polycarboxylic acid are deposited on the surface of a heat transfer in the heat exchanger by decomposition of the amine salt. Moreover, the tubes of the heat exchanger and piping may be occasionally clogged. When the difference in the pressure exceeds the above range, a great energy is required and economic disadvantage arises.

The temperature of the circulating slurry at the outlet of the heat exchanger is made higher than the temperature inside the salt decomposition reactor and the difference in the temperature is, in general, in the range of +1 to +50° C. and preferably in the range of +5 to +20 C. When the difference in the temperature exceeds the above range, side reactions tend to take place in the heat exchanger and the quality of the product is adversely affected. When the difference in the temperature is smaller than the above range, a great amount of the circulating slurry is required to supply the necessary amount of heat, and economic disadvantage arises.

The circulating slurry heated in the heat exchanger is introduced into the salt decomposition reactor after the pressure is reduced by passing through a CV or an orifice. When the length of the piping between the CV or the orifice and the salt decomposition reactor is large, it occasionally takes place that crystals are deposited in the piping before the circulating slurry treated by flushing is introduced into the salt decomposition reactor and the piping is clogged. Therefore, such an arrangement is not preferable. To prevent deposition of the crystals in the piping, it is preferable that the salt decomposition reactor is disposed at a position as close to the CV or the orifice as possible. To prevent sticking and accumulation of the crystals on the wall due to local vaporization, it is preferable that the circulating slurry is introduced into the liquid phase in the salt decomposition reactor.

In the salt decomposition reactor, a mixture of the amine and water is removed by distillation and the amine salt is decomposed while the aromatic polycarboxylic acid is crystallized from the aqueous solution. When the temperature of the salt decomposition reactor is low, the rate of decomposition of the amine salt is small and the ratio of the amount of the amine to the amount of water in the distillate is small. Therefore, it is necessary that a great amount of water be vaporized and economic disadvantage arises. When the temperature of the salt decomposition reactor is high, degradation and coloring of the aromatic polycarboxylic acid take place. Therefore, the temperature of decomposing the salt is, in general, in the range of 100 to 250° C., preferably in the range of 110 to 210° C. and more preferably in the range of 120 to 160° C. The pressure is, in general, in the range of 0 to 2 MPa although the pressure depends on the composition of the content.

In second invention, the decomposition of the salt may be conducted in accordance with a continuous process or a batch process. A continuous process is preferable as the industrial process. When a continuous process is conducted, the steady operation can be achieved by supplying the aqueous solution of the amine salt of the aromatic polycarboxylic acid as the raw material in the same amount as the sum of the amount of the slurry taken out and the amount removed by the distillation. The slurry may be taken out directly from the salt decomposition reactor or from the line of circulation of the circulating slurry.

In the second invention, the particle diameter of the crystallized aromatic polycarboxylic acid can be increased by supplying a small amount of the amine constituting the amine salt into the salt decomposition reactor. As the amine, the amine obtained by decomposing the amine salt may be recovered and used. The position of supply of the amine is not particularly limited. The amine may be supplied directly into the salt decomposition reactor or into the line of circulation of the circulating slurry. It is preferable that the amine is supplied into the line of circulation at a position before the heat exchanger. The amine may be supplied alone or in combination with the aqueous solution of the amine salt or water. The amount of the supplied amine is in the range of 0.01 to 5% by weight and preferably in the range of 0.1 to 2% by weight based on the amount of the crystals of the aromatic polycarboxylic acid in the circulating slurry.

Decomposition of the unreacted amine salt can be accelerated by transferring the slurry taken out of the salt decomposition reactor into a second salt decomposition reactor equipped with a jacket. In the second salt decomposition reactor, heat is supplied from the jacket and the aromatic polycarboxylic acid is crystallized while a mixture of the amine and water is removed by distillation. In this operation, when the temperature of the second salt decomposition reactor is too high, the aromatic polycarboxylic acid and the amine tend to degrade and the crystals tend to deposit and stick to the wall. Therefore, the above operation is conducted at a temperature in the range of 100 to 180° C. and preferably in the range of 110 to 150° C. By suitably controlling the conditions of decomposition of the salt in the second salt decomposition reactor, deposition and sticking of crystals to the wall of the salt decomposition reactor can be suppressed and crystals of the aromatic polycarboxylic acid having a greater particle diameter can be obtained.

Figure 2:
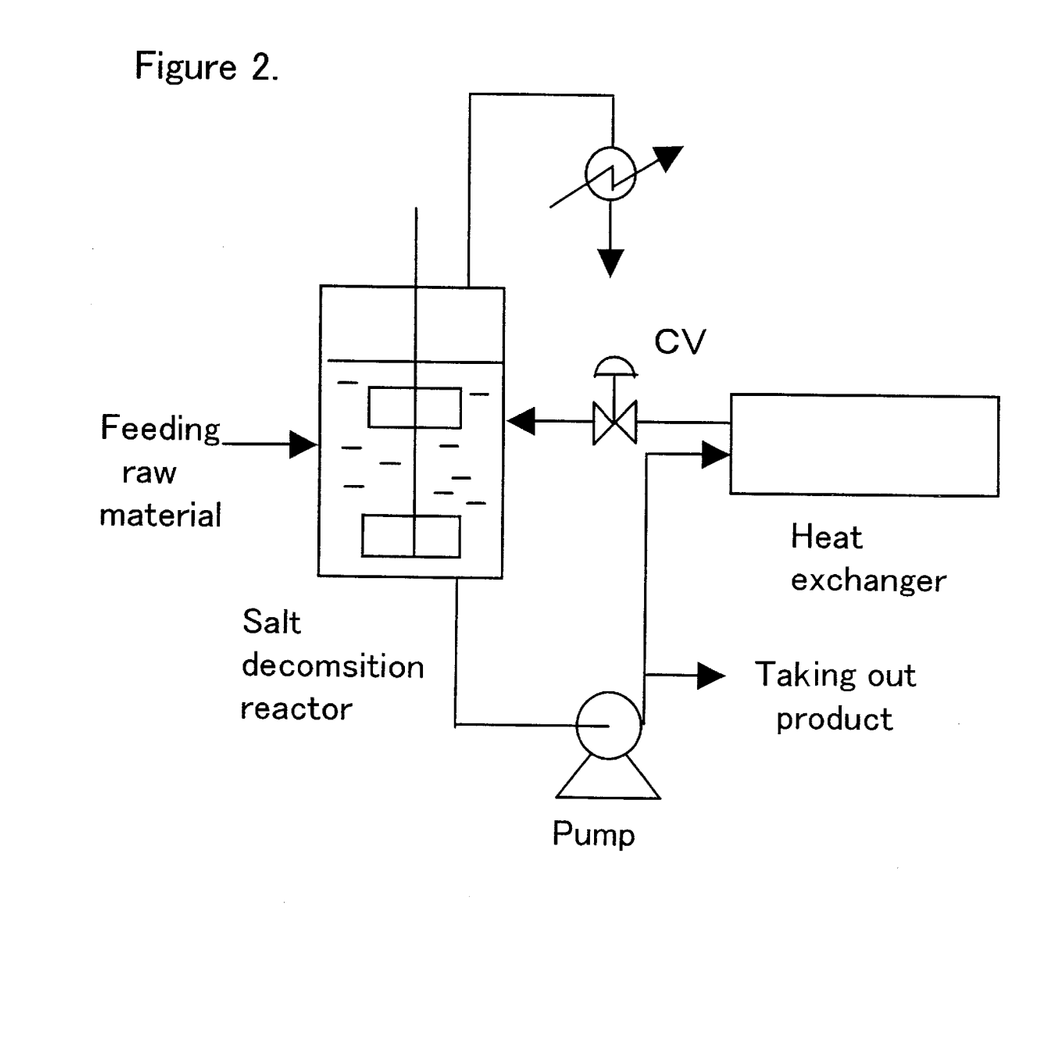
FIG. 2 shows a flow chart exhibiting an embodiment of the process for producing a high purity aromatic polycarboxylic acid of the second invention.

An embodiment of the process of the second invention is shown in FIG. 2. In FIG. 2; the system comprises a salt decomposition reactor, a heat exchanger, a pump and a CV. The pump and the CV is used for circulating the content of the salt decomposition reactor. The slurry in the salt decomposition reactor which comprises an aqueous solution of an amine salt and an aromatic polycarboxylic acid formed by decomposition of the amine salt is circulated by the pump and heated in the heat exchanger. The pressure in the heat exchanger is adjusted by the CV in a manner such that the pressure is kept at the vapor pressure of the slurry or higher. The slurry which is exposed to a reduced pressure and flushed at the outlet of the CV is transferred directly into the salt decomposition reactor. The amine salt is decomposed and the aromatic polycarboxylic acid is crystallized while a mixture of the amine and water are removed by distillation. The position of supply of the raw material and the position of taking out the slurry are not particularly limited.

The slurry containing the crystals of the aromatic polycarboxylic acid obtained in accordance with the process of the second invention is washed and dried, for example, in accordance with the process described in (III) the step of separating crystals in the first invention and crystals of a high purity aromatic polycarboxylic acid which can be used as the raw material for polymers can be obtained.

By decomposing the amine salt of the aromatic polycarboxylic acid in the aqueous solution in accordance with the process of the second invention, the aromatic polycarboxylic acid can be produced continuously for a long time with stability in accordance with the process having a simple construction, as will be described specifically in the following examples.

Therefore, the high purity aromatic polycarboxylic acid can be produced industrially advantageously.

EXAMPLES

The present invention will be described more specifically with reference to examples in the following. However, the present invention is not limited to the examples.

In the following Examples and Comparative Examples, organic impurities in raw materials, an amine salt of an aromatic polycarboxylic acid and crystals of a high purity aromatic polycarboxylic acid were analyzed in accordance with the gas chromatography after being converted into methyl esters.

For the measurement of hue, 1 g of a sample was dissolved in 10 ml of an aqueous solution of sodium hydroxide and the absorption at 400 nm (referred to as $OD_{400}$, hereinafter) of the obtained solution was measured using a 10 mm quartz cell.

The average particle diameter was measured by a wet type particle size distribution meter of the laser diffraction type (HORIBA LA-500).

The "relative amount of steam removed by distillation" means the amount of water distilled in the step of decomposing a salt per unit weight of the obtained aromatic polycarboxylic acid and indicates the energy consumption required for producing a crude aromatic polycarboxylic acid.

The concentration of a slurry and the fraction of decomposition of a salt are as defined above.

The abbreviations used in Examples and Comparative Examples are as follows:

NDCA naphthalenedicarboxylic acid
FNA formylnaphthoic acid
TMAC trimellitic acid
Br-NDCA naphthalenedicarboxyl bromide
NTCA naphthalenetricarboxylic acid
TMA trimethylamine
TEA triethylamine
NDCA-TMA trimethylamine salt of naphthalenedicarboxylic acid
NDCA-TEA triethylamine salt of naphthalenedicarboxylic acid
BPDA biphenyldicarboxylic acid
BPDA-TEA triethylamine salt of biphenyldicarboxylic acid
BPDAIS isomers of biphenyldicarboxylic acid
BPMA biphenylmonocarboxylic acid
TA terephthalic acid
NTECA naphthalenetetracarboxylic acid

Example 1

In an autoclave equipped with a reflux condenser and a tube for measuring the temperature, a crude 2,6-NDCA having the quality shown in the raw material column of Table 1, TEA and water in relative amounts by weight of 1:1:1 were placed and the raw materials were dissolved in water by heating at 80° C. After the resultant solution was cooled to 0° C., formed crystals were filtered through a 5B filter paper and rinsed with acetone and crystals of 2,6-NDCA-TEA were obtained.

The obtained crystals of 2,6-NDCA-TEA and pure water in relative amounts of 2:3 were mixed and the crystals were dissolved in water. Insoluble substances were removed by filtration through a membrane filter of 1 μm and raw material for salt decomposition A (the concentration of NDCA: 20.6%) was obtained.

(Cycle 1)

Into a 1 liter autoclave made of stainless steel and equipped with an outlet for distillates and an outlet for taking out products, 400 g of raw material for salt decomposition A was placed and heated. When the temperature reached 150° C., raw material for salt decomposition A was supplied at a lower portion of the autoclave at a rate of 400 g/hour. At the same time, distillates were removed from the gas phase at a rate of 200 g/hour and a slurry was taken out at a rate of 200 g/hour at 150° C . The continuous decomposition of the salt was conducted for 8 hours in this manner.

The slurry taken out was filtered through a 5B filter paper and crystals were separated from the mother liquor of salt decomposition. The crystals were rinsed with water at 80° C. and dried and a high purity 2,6-NDCA having the quality shown in the column of crystal 1 in Table 1 was obtained. The mother liquor of salt decomposition and the liquid obtained by the rinsing were combined and 90% of the combined liquid was used as mother liquor of salt decomposition 1.

(Cycle 2)

Raw material for salt decomposition A and mother liquor of salt decomposition 1 obtained in cycle 1 in relative amounts by weight of 3:2 were mixed and a raw material for salt decomposition was prepared. The continuous decomposition of the salt and the separation of the crystals were conducted in accordance with the same procedures as those conducted in cycle 1 and a high purity 2,6-NDCA having the quality shown in the column of crystal 2 in Table 1 was obtained. The mother liquor of salt decomposition and the liquid obtained by the rinsing were combined and 90% of the combined liquid was used as mother liquor of salt decomposition 2 in cycle 3.

(Cycle 3)

Raw material for salt decomposition A and mother liquor of salt decomposition 2 obtained in cycle 2 in relative amounts by weight of 3:2 were mixed and a raw material for salt decomposition was prepared. The continuous decomposition of the salt and the separation of the crystals were conducted in accordance with the same procedures as those conducted in cycle 1 and a high purity 2,6-NDCA having the quality shown in the column of crystal 3 in Table 1 was obtained.

In the processes from cycle 1 to cycle 3, the average concentration of the slurry was 21.6% by weight, the fraction of decomposition of the salt was 52.8% and the relative amount of steam removed by distillation was 4.2.

Comparative Example 1

Into a 1 liter autoclave made of stainless steel and equipped with an outlet for distillates and an outlet for taking out products, 400 g of raw material for salt decomposition A obtained in Example 1 was placed and heated. When the temperature reached 150° C., the temperature was maintained. Pure water was supplied at a lower portion of the autoclave at a rate of 200 g/hour. At the same time, distillates were removed at a rate of 200 g/hour. The batch operation for decomposition of the salt was conducted for 3 hours in this manner.

The operation for decomposition of the salt was stopped and the entire amount of the slurry was taken out from the lower portion of the autoclave. The slurry taken out was filtered through a 5B filter paper. The separated crystals were rinsed with water at 80° C. and dried and 72.3 g of 2,6-NDCA having the quality shown in Table 1 was obtained. The yield of NDCA contained in the slurry taken out was 88% based on the amount of the raw material for salt decomposition A.

In the step of decomposing a salt conducted in accordance with the batch process, the concentration of the slurry was 18.1% by weight and the relative amount of steam removed by distillation was 8.4. When the yield was increased in the decomposition of the salt conducted in accordance with the batch process, the relative amount of steam removed by distillation increased and the operation was disadvantageous with respect to energy.

TABLE 1

| Example 1 | (Raw material) | (Crystal 1) | (Crystal 2) | (Crystal 3) | Comparative Example 1 |
|---|---|---|---|---|---|
| 2,6-NDCA (%) | 97.61 | 99.981 | 99.982 | 99.981 | 99.911 |
| TMAC (%) | 1.124 | 0.003 | 0.003 | 0.003 | 0.012 |
| FNA (%) | 0.398 | 0.012 | 0.012 | 0.012 | 0.015 |
| NTCA (%) | 0.283 | 0.002 | 0.001 | 0.001 | 0.008 |
| Br-NDCA (%) | 0.089 | 0.001 | 0.001 | 0.001 | 0.001 |
| $OD_{400}$ | 2.03 | 0.08 | 0.09 | 0.09 | 0.018 |
| Average particle diameter (μm) | 6.3 | 112 | 117 | 105 | 112 |

Example 2

2,6-NDCA-TEA obtained by crystallization in Example 1 and pure water in relative amounts of 1:1 were mixed and 2,6-NDCA was dissolved in pure water. Insoluble substances were removed by filtration through a membrane filter of 1 μm and raw material for salt decomposition B (the concentration of NDCA: 25.8% by weight) was obtained.

(Cycle 1)

Into a 1 liter autoclave made of stainless steel and equipped with an outlet for distillates and an outlet for taking out products, 400 g of raw material for salt decomposition B was placed and heated. When the temperature reached 150° C., raw material for salt decomposition B was supplied at a lower portion of the autoclave at a rate of 400 g/hour. At the same time, distillates were removed from the gas phase at a rate of 250 g/hour and a slurry was taken out at a rate of 150 g/hour at 150° C. The continuous decomposition of the salt was conducted for 8 hours in this manner.

The slurry taken out was filtered through a 5B filter paper and crystals were separated from the mother liquor of salt decomposition. The crystals were rinsed with water at 80° C. and dried and a high purity 2,6-NDCA having the quality shown in the column of crystal 1 in Table 2 was obtained. The mother liquor of salt decomposition and the liquid obtained by the rinsing were combined and 90% of the combined liquid was used as mother liquor of salt decomposition 1.

(Cycle 2)

Raw material for salt decomposition B and mother liquor of salt decomposition 1 obtained in cycle 1 in relative amounts by weight of 1:1 were mixed and a raw material for salt decomposition was prepared. The continuous decomposition of the salt and the separation of the crystals were conducted in accordance with the same procedures as those conducted in cycle 1 and a high purity 2,6-NDCA having the quality shown in the column of crystal 2 in Table 2 was obtained. The mother liquor of salt decomposition and the liquid obtained by the rinsing were combined and 90% of the combined liquid was used as mother liquor of salt decomposition 2.
(Cycle 3)

Raw material for salt decomposition B and mother liquor of salt decomposition 2 obtained in cycle 2 in relative amounts by weight of 1:1 were mixed and a raw material for salt decomposition was prepared. The continuous decomposition of the salt and the separation of the crystals were conducted in accordance with the same procedures as those conducted in cycle 1 and a high purity 2,6-NDCA having the quality shown in the column of crystal 3 in Table 3 was obtained.

In the processes from cycle 1 to cycle 3, the average concentration of the slurry was 45.4% by weight, the fraction of decomposition of the salt was 65.0% and the relative amount of steam removed by distillation was 3.3.

TABLE 2

| Example 2 | (Crystal 1) | (Crystal 2) | (Crystal 3) |
|---|---|---|---|
| 2,6-NDCA (%) | 99.971 | 99.969 | 99.966 |
| TMAC (%) | 0.008 | 0.010 | 0.012 |
| FNA (%) | 0.012 | 0.012 | 0.012 |
| NTCA (%) | 0.005 | 0.005 | 0.006 |
| Br-NDCA (%) | 0.002 | 0.002 | 0.002 |
| $OD_{400}$ | 0.11 | 0.12 | 0.12 |
| Average particle diameter ($\mu$m) | 55 | 53 | 54 |

Example 3

(Cycle 1)

In an autoclave equipped with a reflux condenser and a tube for measuring the temperature, a crude 2,6-NDCA having the quality shown in the raw material column of Table 3, TEA, water and acetone in relative amounts by weight of 1:1:0.6:4 were placed and the mixture was stirred. After the mixture was left standing and cooled to 25° C., crystals of 2.6-NDCA-TEA were formed. The crystals were filtered through a 5B filter paper and rinsed with acetone. The yield of NDCA contained in the crystals of the amine salt was 98% based on the used amount of the crude 2,6-NDCA. The obtained crystals of 2,6-NDCA-TEA and pure water in relative amounts of 2:3 were mixed and the crystals were dissolved in water. The obtained solution was filtered through a membrane filter of 1$\mu$m and used as raw material of salt decomposition 1 (the concentration of NDCA: 20.6% by weight).

Into a 1 liter autoclave made of stainless steel and equipped with an outlet for distillates and an outlet for taking out products, 400 g of raw material for salt decomposition 1 was placed and heated. When the temperature reached 150° C., raw material for salt decomposition 1 was supplied at a lower portion of the autoclave at a rate of 400 g/hour. At the same time, distillates were removed from the gas phase at a rate of 200 g/hour and a slurry was taken out at a rate of 200 g/hour at 150° C. The continuous decomposition of the salt was conducted for 8 hours in this manner.

The slurry taken out was filtered through a 5B filter paper and crystals were separated from the mother liquor of salt decomposition. The crystals were rinsed with water at 80° C. and dried and a high purity 2,6-NDCA having the quality shown in the column of crystal 1 in Table 3 was obtained. The mother liquor of salt decomposition and the liquid obtained by the rinsing were combined and 90% of the combined liquid was used as mother liquor of salt decomposition 1. (The concentration of NDCA: 16.4% by weight and the concentration of TEA: 15.4% by weight).
(Cycle 2)

Mother liquor 1 in an amount of 10% was mixed with the crude 2,6-NDCA, TEA, water and acetone in the same relative amounts as those in cycle 1. The obtained mixture was stirred, filtered and rinsed in 5 accordance with the same procedures as those conducted in cycle 1 and 2,6-NDCA-TEA was obtained. The obtained crystals of 2,6-NDCA-TEA and pure water were mixed in the same relative amounts by weight as those in cycle 1 and crystals of 2,6-NDCA-TEA were dissolved in water. The obtained solution was filtered and used as raw material for salt decomposition 2.

Raw material for salt decomposition 2 and the remaining mother liquor of salt decomposition were mixed and a raw material for salt decomposition was prepared. The continuous decomposition of the salt and the separation of the crystals were conducted in accordance with the same procedures as those conducted in cycle 1 and a high purity 2,6-NDCA having the quality shown in the column of crystal 2 in Table 3 was obtained. The mother liquor of salt decomposition and the liquid obtained by the rinsing were combined and 90% of the combined liquid was used as mother liquor of salt decomposition 2.
(Cycles 3 and further)

2,6-NDCA-TEA was formed using 10% of the mother liquor of salt decomposition obtained in the previous cycle, the crude 2,6-NDCA, TEA, water and acetone in accordance with the same procedures as those in cycle 2. The resultant mixture containing the formed salt was combined with rest of the mother liquor of salt decomposition in the previous cycle and a raw material for salt decomposition was prepared. The continuous decomposition of the salt and the separation of the crystals were conducted in accordance with the same procedures as those conducted in cycle 1. The above procedures were repeated 50 times. When the 50 cycle was completed, a high purity 2,6-NDCA having the quality shown in the column of crystal 50 in Table 3 was obtained.

In the processes from cycle 1 to cycle 10, the average concentration of the slurry was 21.0% by weight, the fraction of decomposition of the salt was 45.0% and the relative amount of steam removed by distillation was 4.3. The yield of NDCA contained in the crystals of the high purity 2,6-NDCA was 94.7% based on the total amount of the crude 2,6-NDCA used in cycles 1 to 50.

It is shown that crystals of the high quality 2,6-NDCA could be easily obtained in a high yield by recycling a portion of the mother liquor in the step of decomposing a salt into the step of forming a salt, concentrating impurities in accordance with the purification process and disposing the impurities.

TABLE 3

| Example 3 | (Raw material) | (Crystal 1) | (Crystal 2) | (Crystal 50) |
|---|---|---|---|---|
| 2,6-NDCA (%) | 98.422 | 99.985 | 99.987 | 99.987 |
| TMAC (%) | 0.620 | 0.001 | 0.001 | 0.000 |
| FNA (%) | 0.264 | 0.011 | 0.008 | 0.008 |
| NTCA (%) | 0.169 | 0.002 | 0.002 | 0.002 |
| Br-NDCA (%) | 0.177 | 0.002 | 0.002 | 0.002 |
| $OD_{400}$ | 1.21 | 0.12 | 0.13 | 0.13 |
| Average particle diameter ($\mu$m) | 6.8 | 112 | 117 | 105 |

Example 4

In an autoclave equipped with a reflux condenser and a tube for measuring the temperature, a crude 4,4'-BPDA shown in the raw material column of Table 4, TMA and water in relative amounts by weight of 1:0.5:3 were placed and the raw materials were dissolved in water by heating at 80° C. under stirring. To the obtained aqueous solution, active carbon powder (manufactured by WAKO JUN'YAKU Co., Ltd.) was added in an amount by weight 1/10 times the amount by weight of the crude 4,4'-BPDA. After being stirred for 30 minutes, the mixture was filtered through a filter paper 5B and raw material of salt decomposition C was obtained (the concentration of 4,4,'-BPDA: 20.1% by weight).

(Cycle 1)

Into a 1 liter autoclave made of stainless steel and equipped with an outlet for distillates and an outlet for taking out products, 400 g of raw material for salt decomposition C was placed and heated. When the temperature reached 150° C., raw material for salt decomposition C was supplied at a lower portion of the autoclave at a rate of 400 g/hour. At the same time, distillates were removed from the gas phase at a rate of 200 g/hour and a slurry was taken out at a rate of 200 g/hour at 150° C. The continuous decomposition of the salt was conducted for 8 hours in this manner.

The slurry taken out was filtered through a 5B filter paper and crystals were separated from the mother liquor of salt decomposition. The crystals were rinsed with water at 80° C. and dried and a high purity 4,4'-BPDA having the quality shown in the column of crystal 1 in Table 4 was obtained. The mother liquor of salt decomposition and the liquid obtained by the rinsing were combined and 90% of the combined liquid was used as mother liquor of salt decomposition 1.

(Cycle 2)

Raw material for salt decomposition C and mother liquor of salt decomposition 1 obtained in cycle 1 in relative amounts by weight of 3:2 were mixed and a raw material for salt decomposition was prepared. The continuous decomposition of the salt and the separation of the crystals were conducted in accordance with the same procedures as those conducted in cycle 1 and a high purity 4,4'-BPDA having the quality shown in the column of crystal 2 in Table 4 was obtained. The mother liquor of salt decomposition and the liquid obtained by the rinsing were combined and 90% of the combined liquid was used as mother liquor of salt decomposition 2.

(Cycle 3)

Raw material for salt decomposition C and mother liquor of salt decomposition 2 obtained in cycle 2 in relative amounts by weight of 3:2 were mixed and a raw material for salt decomposition was prepared. The continuous decomposition of the salt and the separation of the crystals were conducted in accordance with the same procedures as those conducted in cycle 1 and a high purity 4,4'-BPDA having the quality shown in the column of crystal 3 in Table 4 was obtained.

In the processes from cycle 1 to cycle 3, the average concentration of the slurry was 22.2% by weight, the fraction of decomposition of the salt was 55.0% and the relative amount of steam removed by distillation was 3.7.

TABLE 4

| Example 4 | (Raw material) | (Crystal 1) | (Crystal 2) | (Crystal 3) |
| --- | --- | --- | --- | --- |
| 4,4'-BPDA (%) | 96.99 | 99.998 | 99.998 | 99.998 |
| BPDAIS (%) | 0.38 | 0.000 | 0.000 | 0.000 |
| BPMA (%) | 0.18 | 0.001 | 0.001 | 0.001 |
| TA (%) | 1.75 | 0.000 | 0.000 | 0.000 |

TABLE 4-continued

| Example 4 | (Raw material) | (Crystal 1) | (Crystal 2) | (Crystal 3) |
| --- | --- | --- | --- | --- |
| $OD_{400}$ | 2.58 | 0.08 | 0.09 | 0.09 |
| Average particle diameter ($\mu$m) | 25.0 | 108 | 101 | 105 |

Example 5

In an autoclave equipped with a reflux condenser and a tube for measuring the temperature, a crude 1,4,5,8-NTEAC having a purity of 96.8%, TEA and water in relative amounts by weight of 1:1.5:4.5 were placed and the raw materials were dissolved in water by heating at 80° C. under stirring. To the obtained aqueous solution, active carbon powder (manufactured by WAKO JUN'YAKU Co., Ltd.) was added in an amount by weight 1/10 times the amount by weight of the crude 1,4,5,8-NTEAC. After being stirred for 30 minutes, the mixture was filtered through a filter paper 5B and raw material of salt decomposition D was obtained (the concentration of 1,4,5,8-NTEAC: 16.3% by weight).

(Cycle 1)

Into a 1 liter autoclave made of stainless steel and equipped with an outlet for distillates and an outlet for taking out products, 400 g of raw material for salt decomposition D was placed and heated. When the temperature reached 180° C., raw material for salt decomposition D was supplied at a lower portion of the autoclave at a rate of 400 g/hour. At the same time, distillates were removed from the gas phase at a rate of 200 g/hour and a slurry was taken out at a rate of 200 g/hour at 180° C. The continuous decomposition of the salt was conducted for 8 hours in this manner.

The slurry taken out was filtered through a 5B filter paper and crystals were separated from the mother liquor of salt decomposition. The crystals were rinsed with water at 80° C. in an amount 1.5 times the amount of the crystals and dried and a high purity 1,4,5,8-NTEAC. having an average particle diameter of 102 $\mu$m and a purity of 99.88% was obtained. The mother liquor of salt decomposition and the liquid obtained by the rinsing were combined and 80% of the combined liquid was used as mother liquor of salt decomposition 1.

(Cycle 2)

Raw material for salt decomposition D and mother liquor of salt decomposition 1 obtained in cycle 1 in relative amounts by weight of 3:2 were mixed and a raw material for salt decomposition was prepared. The continuous decomposition of the salt and the separation of the crystals were conducted in accordance with the same procedures as those conducted in cycle 1 and a high purity 1,4,5,8-NTEAC. having an average particle diameter of 105 $\mu$m and a purity of 99.87% was obtained. The mother liquor of salt decomposition and the liquid obtained by the rinsing were combined and 80% of the combined liquid was used as mother liquor of salt decomposition 2.

(Cycle 3)

Raw material for salt decomposition D and mother liquor of salt decomposition 2 obtained in cycle 2 in relative amounts by weight of 3:2 were mixed and a raw material for salt decomposition was prepared. The continuous decomposition of the salt and the separation of the crystals were conducted in accordance with the same procedures as those conducted in cycle 1 and a high purity 1,4,5,8-NTEAC. having an average particle diameter of 102 $\mu$m and a purity of 99.86% was obtained.

In the processes from cycle 1 to cycle 3, the average concentration of the slurry was 16.3% by weight, the fraction of decomposition of the salt was 53.5% and the relative amount of steam removed by distillation was 5.5.

From the results in Examples 1 to 5 and Comparative Example 1, the following could be confirmed:

(1) It is shown by the comparison between the results in Example 1 and in Comparative Example 1 that consumption of steam could be decreased and the high quality aromatic polycarboxylic acid could be obtained by conducting the step of decomposing a salt continuously in accordance with the process of the present invention.

(2) Since crystals having a small diameter were obtained in Example 2 in which the concentration of the slurry was increased, it was necessary that the concentration of the slurry in the step of decomposing a salt be kept at a suitable value.

(3) It is shown by the results in Example 3 that crystals of the aromatic polycarboxylic acid could be obtained in a high yield by recycling the mother liquor obtained in the step of separating crystals into the step of decomposing a salt and the step of forming a salt.

(4) It is shown by the results in Examples 4 and 5 that crystals having a high quality could be obtained with small consumption of energy from biphenyldicarboxylic acid (BPDA) and naphthalenetetracarboxylic acid (NTECA) in the same manner as that in the case of naphthalenedicarboxylic acid.

Example 6

In accordance with the flow chart shown in FIG. 2, raw material of salt decomposition A obtained in Example 1, i.e., the aqueous solution of NDCA-TEA having a concentration of NDCA of 20.6% by weight, was fed into a 100 liter salt decomposition reactor equipped with a stirrer, an outlet for taking out a slurry, an outlet for removing distillates and a steam jacket and a heat exchanger of the multi-tubular type (the. area of heat transfer: 3 m$^2$) until the liquid level reached 50% while the solution was circulated by a centrifugal pump.

While the raw material in the salt decomposition reactor was circulated, steam having a saturation temperature of 190° C. was introduced into the heat exchanger and the raw material in the heat exchanger was heated. When the temperature inside the salt decomposition reactor reached 130° C., the speed of circulation of the slurry was set at 4 tons/hour, the rate of feeding the raw material was set at 100 kg/hour and the rate of taking out the slurry was set at 50 kg/hour by controlling the lift of the flow control valve. By controlling the amount of the introduced steam, a mixture of TEA and water was removed by distillation in a manner such that the liquid level was kept constant and the temperature inside the salt decomposition reactor was kept constant at 130° C. The continuous operation in this condition was conducted for 24 hours.

During the operation, the pressure inside the salt decomposition reactor was 0.167 MPa, the temperature at the outlet of the heat exchanger was 138° C. and the pressure at the outlet of the heat exchanger was 0.44 MPa. The slurry taken out was separated into solid components and liquid components. The obtained crystals were washed with water at 80° C. and dried and 225 kg of NDCA having an average particle diameter of 35μm was obtained. Crystals of NDCA stuck to the inner walls of the salt decomposition reactor or the heat exchanger were not found at all.

Comparative Example 2

Into the same 100 liter salt decomposition reactor as that used in Example 6, the same raw material as that used in Example 6 was fed until the liquid level reached 50%. Steam having a saturation temperature of 147° C. was introduced into the jacket of the salt decomposition reactor. When the temperature of the liquid was raised to 130° C., the rate of feeding the raw material was set at 20 kg/hour and the rate of taking out the slurry was set at 10 kg/hour. By controlling the amount of the introduced steam, a mixture of TEA and water was removed by distillation in a manner such that the liquid level was kept constant and the temperature inside the salt decomposition reactor was kept constant at 130° C. The continuous operation in this condition was conducted for 24 hours. The solid-liquid separation and the washing and the drying of the crystals were conducted in accordance with the same procedures as those conducted in Example 6 and 27 kg of NDCA was obtained. The crystals of NDCA were tightly stuck to the inner walls of the salt decomposition reactor and a layer having a thickness of 3 mm was formed.

Example 7

The decomposition of a salt was conducted in accordance with the same procedures as those conducted in Example 6 except that an inverter was disposed in the centrifugal pump and the speed of rotation of the impeller was reduced by 60%. At the outlet of the heat exchanger, the temperature was 138° C. and the pressure was 0.31 MPa. NDCA having a particle diameter of 50 4 μm was obtained in an amount of 225 kg. Crystals of NDCA stuck to the inner walls of the salt decomposition reactor or the heat exchanger were not found at all.

Example 8

Into the same 100 liter salt decomposition reactor and the heat exchanger of the multi-tubular type (the area of heat transfer: 3 m$^2$) as those used in Example 6, the same raw material as that used in Example 7 was fed until the liquid level reached 50% while the raw material was circulated by a centrifugal pump.

Steam having a saturation temperature of 190° C. was introduced into the heat exchanger while the raw material in the salt decomposition reactor was circulated through the heat exchanger by a centrifugal pump. When the temperature inside the salt decomposition reactor reached 150° C., the speed of circulation of the raw material was set at 4 tons/hour, the rate of feeding the raw material was set at 100 kg/hour and the rate of taking out the slurry was set at 50 kg/hour by controlling the lift of the flow control valve. By controlling the amount of the introduced steam, a mixture of TEA and water was removed by distillation in a manner such that the liquid level was kept constant and the temperature inside the salt decomposition reactor was kept constant at 150° C. The continuous operation in this condition was conducted for 24 hours.

During the operation, the pressure inside the salt decomposition reactor was 0.375 MPa, the temperature at the outlet of the heat exchanger was 158° C. and the pressure at the outlet of the heat exchanger was 0.65 MPa. The slurry taken out was separated into solid components and liquid components. The obtained crystals were washed with water at 80° C. and dried and 296 kg of NDCA having an average particle diameter of 55 μm was obtained. Crystals of NDCA stuck to the inner walls of the salt decomposition reactor or the heat exchanger were not found at all.

Example 9

Into the same 100 liter salt decomposition reactor and the heat exchanger of the multi-tubular type (the area of heat transfer: 3 m²) as those used in Example 6, the same raw material as that used in Example 6 was fed until the liquid level reached 50% while the raw material was circulated by a centrifugal pump.

Steam having a saturation temperature of 190° C. was introduced into the heat exchanger while the raw material in the salt decomposition reactor was circulated through the heat exchanger by a pump. When the temperature inside the salt decomposition reactor reached 130° C., the speed of circulation of the raw material was set at 4 tons/hour, the rate of feeding the raw material was set at 100 kg/hour and the rate of taking out the slurry was set at 50 kg/hour by controlling the lift of the flow control valve. By controlling the amount of the introduced steam, a mixture of TEA and water was removed by distillation in a manner such that the liquid level was kept constant and the temperature inside the salt decomposition reactor was kept constant at 130° C. and the continuous decomposition of the salt was conducted in this condition.

The slurry taken out was then transferred to a 20 liter second salt decomposition reactor equipped with a stirrer, an outlet for taking out a slurry, an outlet for distillates and a steam jacket. The slurry was supplied into the second salt decomposition reactor until the liquid level reached 50%. Then, the rate of supply of the slurry was set at 50 kg/hour and the rate of taking out the slurry was set at 45 kg/hour. By controlling the amount of the introduced steam, a mixture of TEA and water was removed by distillation in a manner such that the liquid level was kept constant and the temperature inside the salt decomposition reactor was kept constant at 120° C. The continuous operation was conducted in this condition for 24 hours. During the operation, the pressure inside the second salt decomposition reactor was 0.09 MPa. The obtained crystals were washed with water at 80° C. and dried and 270 kg of NDCA having an average particle diameter of 70 μm was obtained. Crystals of NDCA stuck to the inner walls of the second salt decomposition reactor were not found at all.

Example 10

Into the same 100 liter salt decomposition reactor and the heat exchanger of the multi-tubular type (the area of heat transfer: 3 m²) as those used in Example 6, an aqueous solution of BPDA-TEA (the concentration of BPDA: 21.8% by weight) as the raw material was fed until the liquid level reached 50% while the raw material was circulated by a centrifugal pump.

Steam having a saturation temperature of 190° C. was introduced into the heat exchanger while the raw material in the salt decomposition reactor was circulated through the heat exchanger by a pump. When the temperature inside the salt decomposition reactor reached 130° C., the speed of circulation of the raw material was set at 2 tons/hour, the rate of feeding the raw material was set at 100 kg/hour and the rate of taking out the slurry was set at 50 kg/hour by controlling the lift of the flow control valve. By controlling the amount of the introduced steam, a mixture of TEA and water was removed by distillation in a manner such that the liquid level was kept constant and the temperature inside the salt decomposition reactor was kept constant at 130° C. The continuous operation in this condition was conducted for 24 hours.

During the operation, the pressure inside the salt decomposition reactor was 0.167 MPa, the temperature at the outlet of the heat exchanger was 146° C. and the pressure at the outlet of the heat exchanger was 0.52 MPa. The slurry taken out was separated into solid components and liquid components. The obtained crystals were washed with water at 80° C. and dried and 314 kg of BPDA having an average particle diameter of 40 μm was obtained. Crystals of BPDA stuck to the inner walls of the salt decomposition reactor or the heat exchanger were not found at all.

Example 11

Into the same 100 liter salt decomposition reactor and the heat exchanger of the multi-tubular type (the area of heat transfer: 3 m²) as those used in Example 6, an aqueous solution of NDCA-TMA (the concentration of NDCA: 25.8% by weight) as the raw material was fed until the liquid level reached 50% while the raw material was circulated by a centrifugal pump.

Steam having a saturation temperature of 190° C. was introduced into the heat exchanger while the raw material in the salt decomposition reactor was circulated through the heat exchanger by a pump. When the temperature inside the salt decomposition reactor reached 130° C., the speed of circulation of the raw material was set at 4 tons/hour, the rate of feeding the raw material was set at 100 kg/hour and the rate of taking out the slurry was set at 50 kg/our by controlling the lift of the flow control valve. By controlling the amount of the introduced steam, a mixture of TMA and water was removed by distillation in a manner such that the liquid level was kept constant and the temperature inside the salt decomposition reactor was kept constant at 130° C. The continuous operation in this condition was conducted for 24 hours.

During the operation, the pressure inside the salt decomposition reactor was 0.170 MPa, the temperature at the outlet of the heat exchanger was 138° C. and the pressure at the outlet of the heat exchanger was 0.45 MPa. The slurry taken out was separated into solid components and liquid components. The obtained crystals were washed with water at 80° C. and dried and 433 kg of NDCA having an average particle diameter of 32 μm was obtained. Crystals of NDCA stuck to the inner walls of the salt decomposition reactor or the heat exchanger were not found at all.

What is claimed is:

1. A process for producing a high purity aromatic polycarboxylic acid by purifying a crude aromatic polycarboxylic acid in accordance with (I) a step of forming a salt which comprises forming an amine salt of an aromatic polycarboxylic acid from the crude polycarboxylic acid and an amine, (II) a step of decomposing a salt which comprises (i) conducting in a salt decomposition reactor operations of supplying an aqueous solution of the amine salt of an aromatic polycarboxylic acid formed in the step of forming a salt, (ii) removing the amine and water by distillation under heating and (iii) taking out a slurry containing crystallized aromatic polycarboxylic acid, and (III) a step of separating crystals which comprises separating and recovering crystals of the aromatic polycarboxylic acid from the slurry which is taken out in the step of decomposing a salt, wherein in the step of decomposing a salt, the slurry in the salt decomposition reactor which comprises the aqueous solution of the amine salt and the aromatic polycarboxylic acid formed by the decomposition is circulated through a heat exchanger, heat is supplied in the heat exchanger while a pressure of the slurry is kept at a vapor pressure of the slurry or higher, wherein the pressure of the slurry in the heat exchanger being kept higher than the vapor pressure of the slurry at a temperature at an outlet of the heat exchanger and a difference in the pressure being in a range of +0.02 MPa to +0.5 MPa, a mixture of the amine and water is removed by distillation in the salt decomposition reactor, and the aromatic polycarboxylic acid is crystallized in the salt decomposition reactor.

2. A process according to claim 1, wherein the slurry is circulated by a pump.

3. A process according to claim 2, wherein a speed of rotation of an impeller in the pump is controlled by an inverter.

4. A process according to claim 1, wherein a pressure inside the heat exchanger is controlled by a control valve.

5. A process according to claim 1, wherein a linear velocity of the slurry passing through the heat exchanger is 1 m/sec or greater.

6. A process according to claim 1, wherein a temperature of the slurry in the salt decomposition reactor is in a range of 120 to 160° C.

7. A process according to claim 1, wherein a temperature of the slurry at an outlet of the heat exchanger is higher than a temperature inside the salt decomposition reactor and a difference in the temperature is in a range of +5 to +20° C.

8. A process according to claim 1, herein an amine of a same type as the amine forming the amine salt of the polycarboxylic acid is fed into a circulating line of the slurry.

9. A process according to claim 1, wherein the slurry is taken out from the salt decomposition reactor; the slurry is supplied into a second salt decomposition reactor having a jacket and heated; and the unreacted amine salt is decomposed.

10. A process according to claim 1, wherein the aromatic polycarboxylic acid as a component of the amine salt of the polycarboxylic acid is a compound selected from naphthalenepolycarboxylic acids and biphenylpolycarboxylic acids.

11. A process according to claim 1, wherein the amine as a component of the amine salt of the polycarboxylic acid is at least one amine selected from aliphatic amines and alicyclic amines.

12. A process according to claim 1, wherein the amine as a component of the amine salt of the aromatic polycarboxylic acid is a compound selected from triethylamine and trimethylamine.

13. A process according to claim 1, wherein heat is supplied in the heat exchanger while pressure of the slurry is kept at a vapor pressure of the slurry or higher, such that decomposition of the amine salt in the heat exchanger is suppressed and adherence of the aromatic polycarboxylic acid to tubes of the heat exchanger and piping is suppressed.

14. A process according to claim 3, wherein said inverter controls speed of rotation of the impeller so that fracture of crystals of the aromatic carboxylic acid is suppressed.

* * * * *